United States Patent
Di Berardino et al.

(10) Patent No.: US 10,987,257 B2
(45) Date of Patent: Apr. 27, 2021

(54) APPARATUS AND METHOD OF MANUFACTURING OF AN ABSORBENT ELEMENT FOR SANITARY PRODUCTS

(71) Applicant: TEXOL S.R.L., Alanno (IT)

(72) Inventors: Marino Di Berardino, Roccamontepiano (IT); Fabio Di Berardino, Roccamontepiano (IT)

(73) Assignee: TEXOL S.R.L., Alanno (IT)

( * ) Notice: Subject to any disclaimer, the term of this patent is extended or adjusted under 35 U.S.C. 154(b) by 345 days.

(21) Appl. No.: 16/080,484

(22) PCT Filed: Mar. 2, 2017

(86) PCT No.: PCT/IB2017/051216
§ 371 (c)(1),
(2) Date: Aug. 28, 2018

(87) PCT Pub. No.: WO2017/149487
PCT Pub. Date: Sep. 8, 2017

(65) Prior Publication Data
US 2019/0060141 A1    Feb. 28, 2019

(30) Foreign Application Priority Data
Mar. 2, 2016 (IT) .......... 102016000021714

(51) Int. Cl.
*A61F 13/53* (2006.01)
*A61F 13/532* (2006.01)
(Continued)

(52) U.S. Cl.
CPC .... *A61F 13/5323* (2013.01); *A61F 13/15658* (2013.01); *A61F 13/15699* (2013.01);
(Continued)

(58) Field of Classification Search
CPC ............ A61F 13/15642; A61F 13/1565; A61F 13/15658; A61F 13/16599;
(Continued)

(56) References Cited

U.S. PATENT DOCUMENTS 8,180,603 B2 * 5/2012 Blessing ............... B05C 1/0817
703/2
8,633,347 B2 * 1/2014 Bianco ................ A61F 13/5323
604/378

(Continued)

FOREIGN PATENT DOCUMENTS

EP    0875224 A1    11/1998
EP    1974705 A1    10/2008
(Continued)

OTHER PUBLICATIONS

International Search Report and Written Opinion for Corresponding International Application No. PCT/IB2017/051216 (14 Pages) (dated May 24, 2017).

*Primary Examiner* — Catharine L Anderson
(74) *Attorney, Agent, or Firm* — Lucas & Mercante LLP (57) ABSTRACT

An apparatus for manufacturing an absorbent element for sanitary products and a method for manufacturing the same are disclosed. The absorbent element is of the type incorporating plurality of sacs or pockets in which expandable super-absorbent material is placed.

23 Claims, 5 Drawing Sheets

(51) Int. Cl.
*A61F 13/15* (2006.01)
*A61F 13/533* (2006.01)
*B32B 3/30* (2006.01)
*B29C 59/04* (2006.01)
*B32B 3/26* (2006.01)
*B32B 5/02* (2006.01)
*B32B 27/08* (2006.01)

(52) U.S. Cl.
CPC .. *A61F 13/15707* (2013.01); *A61F 13/15731* (2013.01); *A61F 13/533* (2013.01); *B32B 3/30* (2013.01); *A61F 2013/15926* (2013.01); *A61F 2013/53051* (2013.01); *A61F 2013/530481* (2013.01); *A61F 2013/530562* (2013.01); *B29C 59/04* (2013.01); *B32B 3/266* (2013.01); *B32B 5/022* (2013.01); *B32B 27/08* (2013.01); *B32B 2307/726* (2013.01); *B32B 2555/02* (2013.01)

(58) Field of Classification Search
CPC ............ A61F 13/15731; A61F 13/5323; A61F 13/533; A61F 2013/15926; A61F 2013/530481; A61F 2013/53051; A61F 2013/530547; A61F 2013/530554; A61F 2013/530562
See application file for complete search history.

(56) References Cited

U.S. PATENT DOCUMENTS

| | | | | |
|---|---|---|---|---|
| 8,646,506 | B2* | 2/2014 | Ukegawa | A61F 13/15658 |
| | | | | 156/553 |
| 9,308,132 | B2* | 4/2016 | Nakakado | A61F 13/15699 |
| 9,456,929 | B2* | 10/2016 | Maruhata | B05C 19/00 |
| 9,532,906 | B2* | 1/2017 | Bauduin | A61F 13/538 |
| 9,956,586 | B2* | 5/2018 | Pinyayev | B32B 27/10 |

FOREIGN PATENT DOCUMENTS

| | | |
|---|---|---|
| EP | 2540266 A1 | 1/2013 |
| EP | 2586409 A1 | 5/2013 |
| WO | 2006077611 A1 | 7/2006 |

\* cited by examiner

APPARATUS AND METHOD OF MANUFACTURING OF AN ABSORBENT ELEMENT FOR SANITARY PRODUCTS

CROSS-REFERENCE TO RELATED APPLICATIONS

This application is a 371 of PCT/IB2017/051216, filed Mar. 2, 2017, which claims the benefit of Italian Patent Application No. 102016000021714, filed Mar. 2, 2016.

TECHNICAL FIELD OF THE INVENTION

The present invention relates to an absorbent element for sanitary products and to an apparatus and a method for manufacturing such element.

In particular, the absorbent element is of the type incorporating a plurality of sacs or pockets wherein an expandable super-absorbent material is received.

BACKGROUND

On the market there are several sanitary articles with absorbent function, for example diapers for babies, products for senile and light incontinence, absorbent products for women, as well as medical products in general.

The effectiveness and the use comfort of such articles depend in a decisive way upon the absorbent and storage capabilities thereof, to avoid the need for too frequent changes or unwished liquid leaks. In the last decade so-called "super-absorbent" materials, in particular the so-called "SAP" (Super-Absorbent Powders), have been developed, having the capability of absorbing the liquid by increasing the volume thereof.

However, the potentiality for using such materials are not wholly exploited. This due to the limits of the current absorbent elements in allowing a complete expansion of the super-absorbent component and, then, the whole use of the maximum absorbance thereof, however while keeping a stable structure of the element as a whole and the use comfort.

SUMMARY OF THE INVENTION

The technical problem placed and solved by the present invention is therefore to provide an absorbent element and consequent capability of storage of body fluids, for a sanitary article allowing to obviate the drawbacks mentioned above with reference to the known art.

Such problem is solved by an absorbent element according to claim 1.

The invention further provides a method for manufacturing said absorbent element according to claim 18 and a related apparatus according to claim 12.

Preferred features of the present invention are set forth in the depending claims.

The invention provides an absorbent element having an improved structure and allowing a full expansion of a super-absorbent material contained inside thereof.

At the same time, the direct contact of the absorbent element with the subject's skin can be avoided.

In this way, the absorbent element optimizes the use of the super-absorbent material in terms of quantity and quality.

The absorbent element further guarantees the reliability and the use comfort of the sanitary article in which it is incorporated.

Other advantages, features and use modes of the present invention will result evident from the following detailed description of some embodiments, shown by way of example and not for limitative purposes.

BRIEF DESCRIPTION OF FIGURES

The figures of the enclosed drawings will be referred to, wherein.

DETAILED DESCRIPTION OF PREFERRED EMBODIMENTS

Several embodiments and variants of the invention will be described hereinafter and this by referring to the above-mentioned figures.

Analogous components are designated in the different figures with the same numeral reference.

In the following detailed description, additional embodiments and variants, with respect to embodiments and variants already treated in the same description, will be illustrated limitedly to the differences with respect to what already shown.

Furthermore, the different embodiments and variants described hereinafter can be used in combination, if compatible.

Figure 1A:
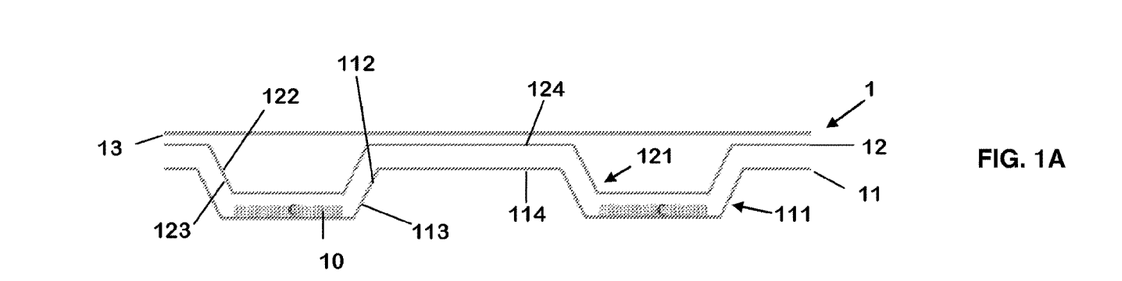
FIGS. 1A and 1B relate to a first preferred embodiment of an absorbent element according to the present invention, each one showing an exemplifying schematic cross section view thereof, in a rest configuration and a maximum absorption configuration, respectively.

By firstly referring to FIG. 1A, an absorbent element for biological liquids according to a first embodiment of the invention is designated as a whole with 1.

The absorbent element 1 is suitable to be incorporated in a sanitary article, for example a diaper for babies or, generally, for incontinence.

In the present embodiment, the absorbent element 1 is substantially in form of multilayer sheet.

In particular, the absorbent element 1 comprises a first layer of laminate material 11, having a plurality of first cavities, or sacs, each one designated with 111.

Each first cavity 111 has a concave face, or concavity, 112 and a convex face, or convexity, 113 opposite to the concave face 112.

At the bottom of the cavity 111 a mass 10 of superabsorbent material C is received. The latter, in the present example, is a material in powder or granules. In particular, the material can be a cross-linked polyacrilate-based polymer soluble in water with additional organic elements. Additionally, different types of powders or granules can be used which, apart from the main feature of absorbing fluids, have even that of absorbing and/or neutralizing bad smells or providing for the product perfuming. The materials as base substances can have silica, zeolite, chitin and/or chitosan or other.

The absorbent element 1 further comprises a second layer of laminate material 12. The latter has a plurality of second cavities, or sacs, each one designated with 121. Each second cavity 121 has a concave face, or concavity, 122 and a convex face, or convexity, 123 opposite to the concave face 122.

Each second cavity 121 is arranged within a respective first cavity 111 and so that the convexity 123 thereof faces the concavity 112 of the first cavity 111 and then the respective super-absorbent material mass 10 received therein.

Therefore, each first cavity 111 cooperates with a second cavity 121 to define a seat which receives the respective super-absorbent material mass 10. The latter is then housed on the bottom of the concave face 112 of the first cavity 111 and closed by the bottom of the convex face 123 of the second cavity 121.

In the present example, the first and the second cavities 111 and 121 have the same profile. In particular, they have as a whole a circular-plan geometry, with tapered, in particular frusto-conical, cross section, with section decreasing towards its own bottom.

Embodiment variants can provide a cylindrical geometry for one or both cavities.

The first and the second laminate material layer 11 and 12 are fixed to one another at least at respective intermediate longitudinal portions 114, 124 devoid of cavities 111, 121.

In the present embodiment, the absorbent element 1 even comprises a third laminate material layer 13 coupled to the second layer 12 on the side opposite to the coupling of the latter with the first layer 11. In other words, the configuration is such that the second layer 12 is received with sandwich-like arrangement between the first and the third layer 11 and 13.

The above-mentioned couplings among layers 11, 12 and 13 can be obtained by means of an adhesive and in case hot performed.

Moreover, the formation of cavities in the materials can be obtained by thermoforming.

Figure 1B:
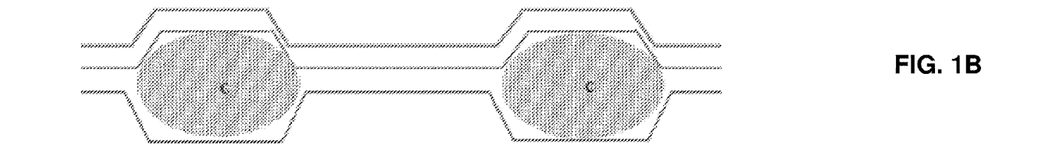

As shown in FIG. 1B, in use the masses of super-absorbent material 10 absorb the biological liquid, by expanding and deforming the respective second cavities 121 up to overturn the concavity/convexity 122/123 thereof.

In the present example, even the third layer 13 results to be deformed to follow the overturned profile of the second cavities 121.

The space left empty inside the cavities when the absorbent element is under dry conditions can take into consideration a swelling ratio of the dry/wet material C. The latter, for example, on the average is 1:25 (1 gr of SAP can absorb 25 gr of liquid, with clear increase in the volumetric mass).

The material of the first layer 11, of the second layer 12 and/or of the third layer 13 can be selected in a group comprising polymeric materials and natural materials. The material structure can be that of the elastic, nonwoven and/or perforated materials, for example with microholes with diameter comprised in a range of 0.2-5.0 mm and density of about 100 holes/cm$^2$.

Figure 2A:
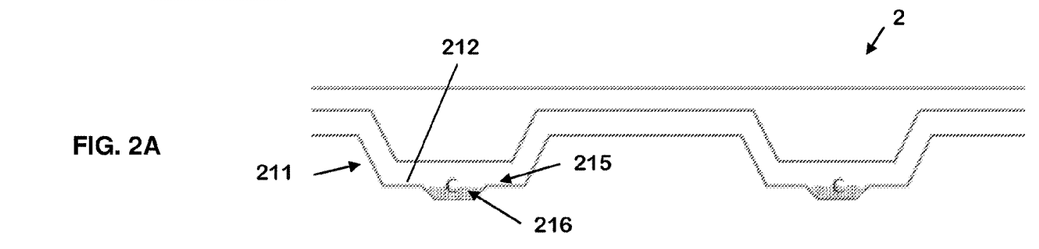
FIGS. 2A and 2B relate to a second preferred embodiment of an absorbent element according to the present invention, each one showing an exemplifying schematic cross section view thereof, in a rest configuration and a maximum absorption configuration, respectively.
Figure 2B:
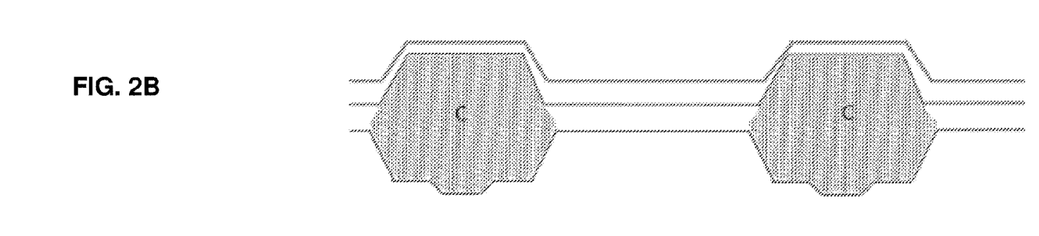

By referring to FIGS. 2A and 2B, an absorbent element implemented based upon a second preferred embodiment of the invention is designated as a whole with 2.

In this case, each first cavity, herein designated with 211, has a double-sac profile. In particular, it defines, at its own concave face 212, a main compartment 215 and a secondary compartment 216. In the present example, the latter defines a sub-portion of the main compartment 215 at the bottom of the cavity 211.

Preferably, under conditions of not absorption, the respective super-absorbent material mass 10 is wholly, or almost wholly, received in the secondary compartment 216.

Preferably, the secondary compartment 216 is arranged centrally in the main compartment 215.

In the present embodiment, even the compartment 216 has substantially frusto-conical geometry.

Figure 3A:
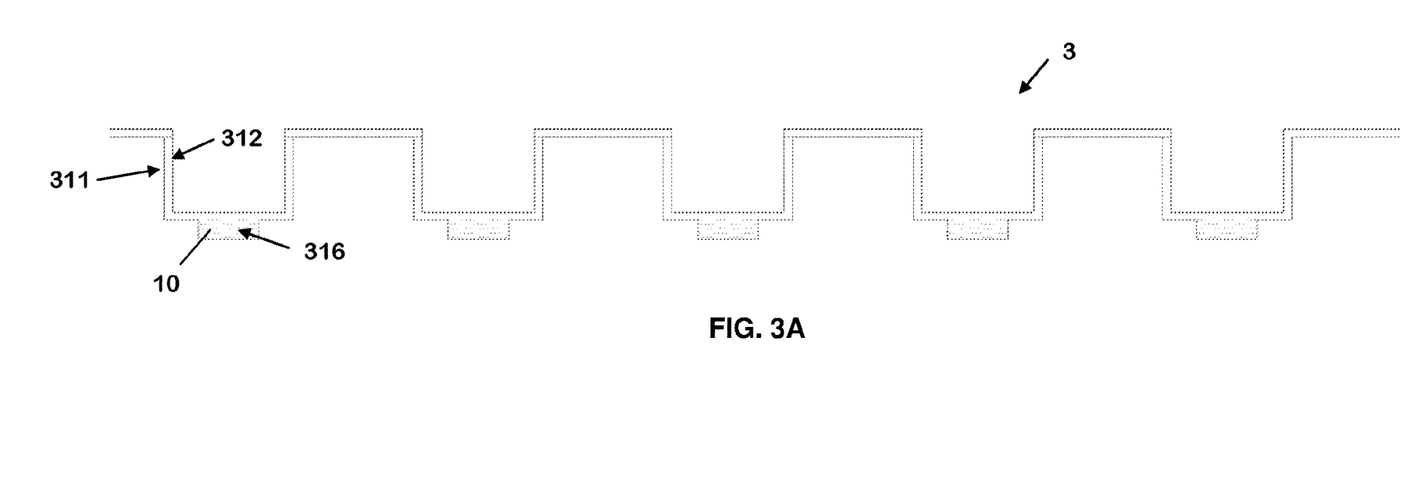
FIGS. 3A, 3B and 3C relate to a third preferred embodiment of an absorbent element according to the present invention, each one showing an exemplifying schematic cross section view thereof, in a rest configuration, a first maximum absorption configuration and a second possible maximum absorption configuration, respectively.

FIG. 3A relates to a third embodiment of an absorbent element according to the invention, in this case designated as a whole with 3. Differently from the second embodiment, the absorbent element 3 has each secondary compartment, herein designated with 316, with substantially cylindrical geometry. Similarly the geometry of the respective first cavity, herein designated with 311, and of the respective second cavity, herein designated with 312, is cylindrical too.

Even if not represented, the absorbent element 3 too can have a third laminate material layer, analogously to what illustrated in relation to the preceding embodiments.

Figure 3B:
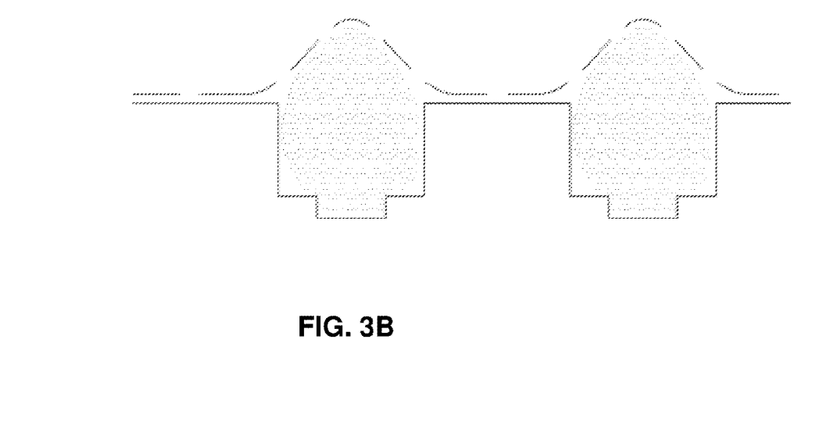
Figure 3C:
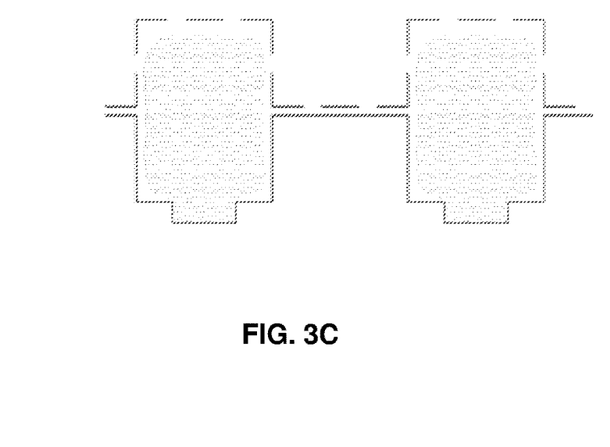

FIGS. 3B and 3C show, each one, a respective possible mode of expansion, in use, of the masses 10 in the absorbent element 3.

Figure 4:
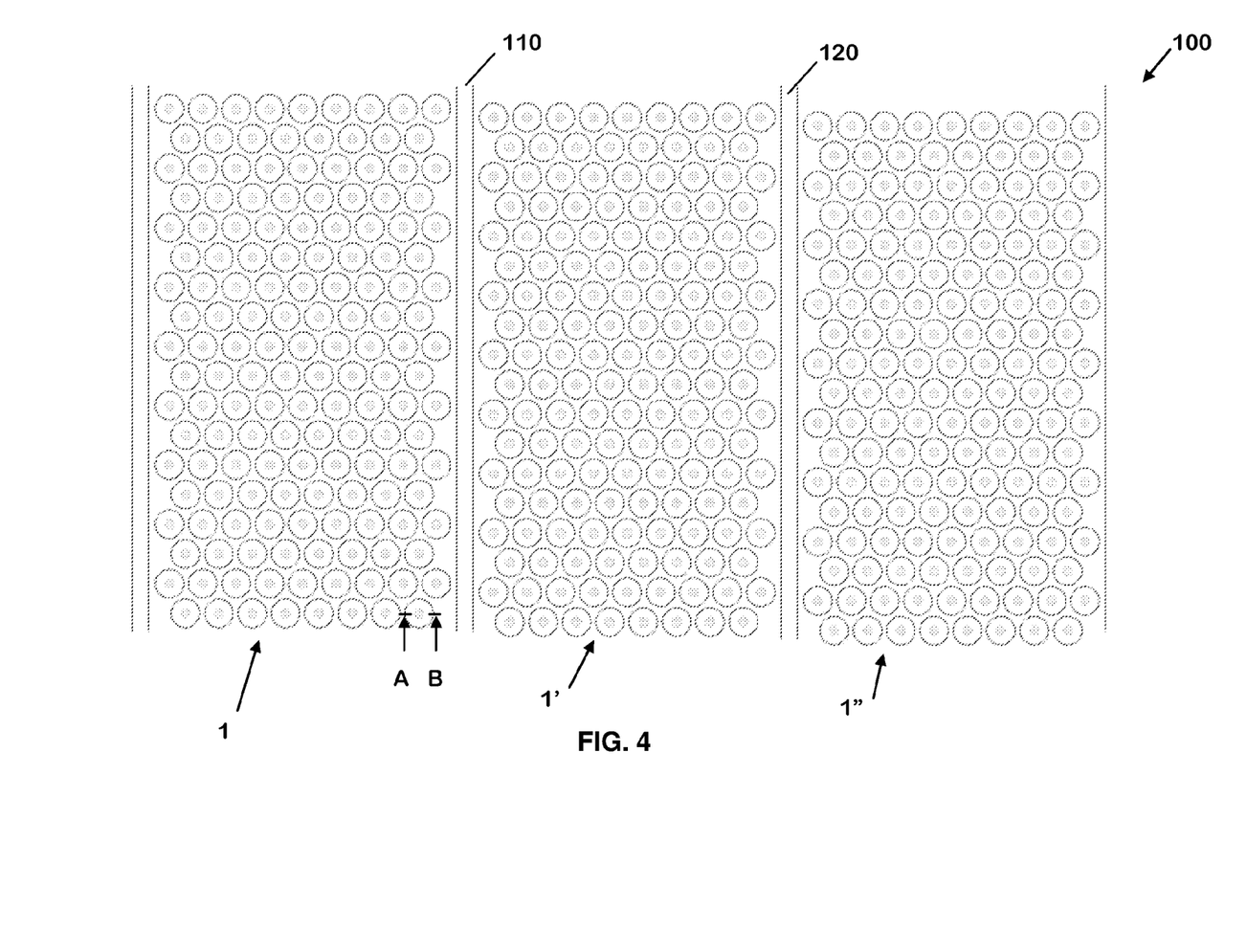
FIG. 4 shows an exemplifying schematic top view of the absorbent element of the preceding figures, highlighting in transparency the presence of a super-absorbent material and wherein line A-B designates a section plane used in the preceding figures.

By referring to FIG. 4, the absorbent element 1 is shown connected to analogous absorbent elements 1' and 1" to form a composite structure 100. In the latter, several absorbent elements 1, 1' and 1" are placed side by side and connected at their own side margins 110, 120 devoid of cavities.

An analogous structure can be obtained by means of the absorbent elements designated with 2 and 3 in the other embodiments or even by means of a combination of the elements 1, 2 and 3.

Figure 5:
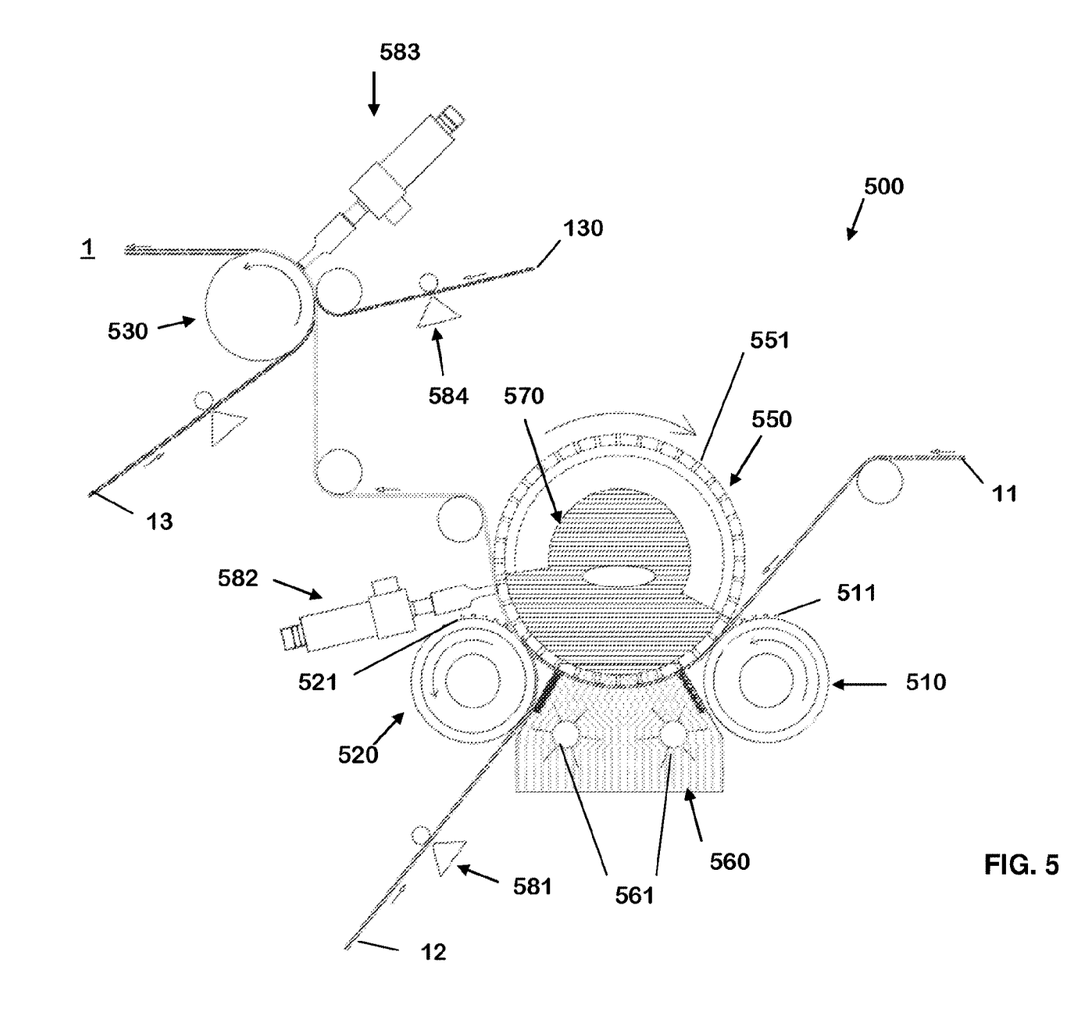
FIG. 5 shows an exemplifying schematic representation of a side view of a preferred embodiment of an apparatus for manufacturing the absorbent element of FIG. 1A.

By referring to FIG. 5, an apparatus for manufacturing the above-described absorbent element 1 according to a preferred embodiment is designated as a whole with 500.

The laminate materials constituting the first, the second and the third layer 11, 12 and 13 mentioned above are fed to the apparatus 500 and within the latter. For sake of simplicity, such materials are herein designated with the same reference numeral of the layer which they are going to implement. Such feeding takes place by means of known means, for example idler and/or feeding rollers shown schematically in figure, which will not further described.

The apparatus 500 implements the absorbent element 1 by means of a sequence of steps for embossing and coupling the laminate materials.

In particular, the apparatus 500 comprises a first embossing roller 510, having a plurality of first protruding, or embossing, elements 511 and configured to be engaged, in use, by the first laminate material 11.

The first embossing roller 510 cooperates with a suction roller 550 coupled thereto according to the rotation directions designated in figure. The suction roller 550 comprises a plurality of openings, or holes or seats, 551 each one suitable for receiving a respective protruding element 511 of the first roller 510.

The configuration then is such that the first protruding elements 511 and the openings 551 cooperate to implement in the material 11 the first cavities 111 of the absorbent element 1. In particular, during the related rotation one protruding element 511 at a time engages an opening 551 with interposition of the material 11.

The suction roller 550 has, or it is associated to, suction means 570 operating through a portion of the openings 551 to exert a suction action. In particular, such suction is exerted at one or more openings which, in use, are facing a reservoir, or tank, 560 of super-absorbent material C.

The reservoir 560 is arranged downstream of the first embossing roller 510 with respect to the mutual rotation thereof and of the suction roller 550.

Preferably, within the reservoir 560 mixing means 561 is provided, based for example upon a pair of rotating elements with axis parallel to the rotation axis of the rollers. Such mixing means can provide stirring elements or rotating paddles.

The suction roller 550 remains always plunged into the reservoir 560, by guaranteeing the correct and continuous suction of the material C.

The reservoir 560 further remains always full and is constantly supplied, for example by gravity.

As said above, the suction system is divided into areas: only in the area wherein the cavities 111 form, the void is activated thanks to the presence of a perforated grid allowing the suction.

Thanks to the suction action, the masses 10 of super-absorbent material C are sucked into the respective first cavities 111 just formed into the first material 11.

Downstream of the reservoir 560 a second embossing roller 520 is provided, having a plurality of second protruding, or embossing, elements 521. Even the second roller 520 engages in mutual rotation the suction roller 550, so that in the related rotation one protruding element 511 at a time engages an opening 551. Such engagement takes place with interposition of the material 11 and of the material 12 which is fed to the second roller 520. In this way, on the second material 12 the second cavities 121 are implemented.

In the present example, the configuration of the embossing protruding elements 511 and 521 and that of the openings 551 is so as to determine the above-described frusto-conical shape of the cavities 111 and 121.

Upstream of the first or of the second embossing roller 510, 520 a doctor blade, or equivalent means, can be provided for cleaning the possible super-absorbent material which has deposited outside the cavities 111. The material C removed by such doctor blade can fall again into the reservoir 560 for subsequent re-use.

In the present embodiment a third roller 530 to which the third laminate material 13 is fed is further provided.

The apparatus 500 further comprises a unit 581 for depositing glue on the second material 12, arranged upstream of the second embossing roller 520. The unit 581 can use an adhesive of the so-called "hot melt" type.

Alternatively to the applicator of "hot melt" glues, a hot calender ultrasound system can be used.

The apparatus 500 further comprises a unit 582 for coupling the first and the second material 11 and 12, preferably arranged downstream of the second embossing roller 520. Such unit 582 can operate for example by means of ultrasound lamination.

An analogous unit, designated with 583, can be provided for coupling the third laminate material 13 to the remaining structure.

The apparatus 500 then includes means for adjusting the relative distance among the various rollers, in particular among the rollers 510, 520 and 550, even to vary the penetration depth of the protruding elements 511, 521 within the openings 551.

Based upon an embodiment variant represented in FIG. 5, a fourth laminate material 130 can be provided, coupled to the remaining structure, in particular on the first layer 11 on the opposite side with respect to the second layer 12.

In the shown example, the coupling takes place by means of "hot melt" gluing, with adhesive fed on the material 130 in a unit 584 and subsequent passage in the unit 583.

The materials 13 and 130 can even be the same.

In the described configuration, all rollers, and in particular those designated with 510, 520, 550 and preferably 530, have parallel rotation axes.

Moreover, one or more rollers can be motorized in an independent way, for example by means of brushless motors and precision reducing means.

One or more rollers, in particular the suction roller 550, can be made of metal (generally of bronze and/or the like).

The pitch and the diameter of the openings 551 and of the protruding elements 511 and 521 are determined based upon the end features, in particular the absorbance, requested by the absorbent element to be implemented.

In an implementing example, each opening 551 has diameter equal to about 3-4 mm with pitch between hole and hole (measured as circumference cord) of about 4-5 mm.

In order to guarantee the correct temperature to the production process, one or more rollers can be controlled in temperature.

Such temperature control can even allow a forming by thermoforming of cavities 111 and/or 121.

Figure 6:
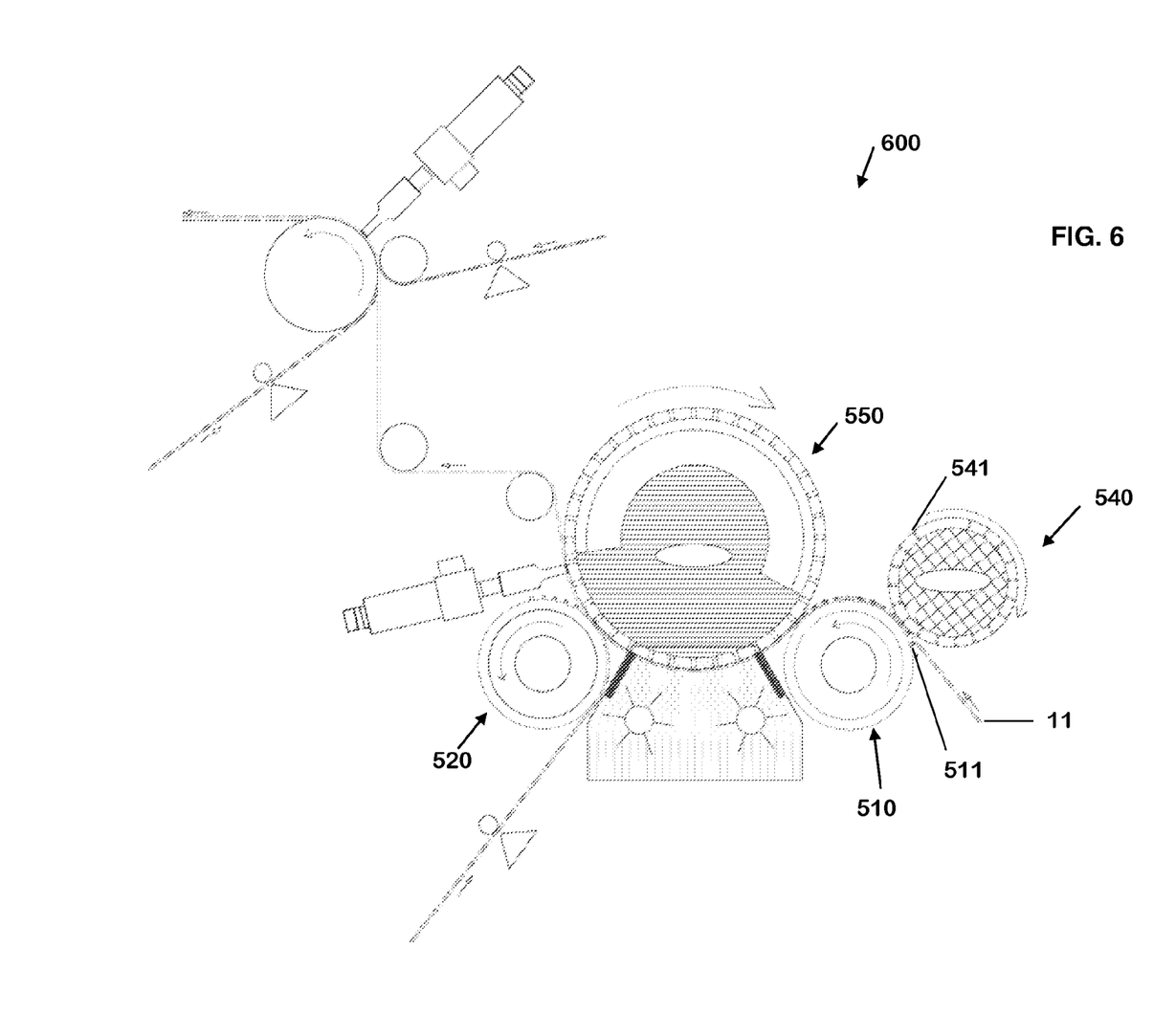
FIG. 6 shows an exemplifying schematic representation of a side view of a preferred embodiment of an apparatus for manufacturing the absorbent element of FIG. 2A or 3A.

FIG. 6 shows a preferred embodiment of an apparatus for manufacturing the above-described absorbent element 2, which apparatus is designated as a whole with 600.

With respect to the apparatus 500 of the preceding embodiment, the apparatus 600 further comprises an auxiliary roller 540, coupled to the first embossing roller 510 upstream of the suction roller 550.

The auxiliary roller 540 has a plurality of auxiliary openings 541, each one suitable for receiving a first protruding element 511 of the first roller 510 during the related coordinated rotation of the two rollers.

In particular, the configuration is so that such coupling between elements 511 and openings 541 takes place with interposition of the first laminate material 11 upstream of the implementation of the first cavities 111 thereon.

In the present example, the configuration of the embossing protruding elements 511 and 521 and that of the openings 551 and 541 is so as to determine the above-mentioned frusto-conical shape of cavities and compartments of the absorbent element 2.

Embodiment variants can provide the implementation of the absorbent element 3 with cylindrical geometry cavities.

In general terms, the shape of the cavities obtained in the end absorbent element can be adjusted by means of the shaping of the protruding elements and/or of the openings and/or by means of the mutual distance and arrangement thereof.

The present invention has been so far described with reference to preferred embodiments. It is to be meant that other embodiments may exist, all belonging to the same inventive core, as defined by the protection scope of the here below reported claims.

The invention claimed is:

1. An absorbent element configured for absorbing biological liquids and configured to be incorporated in a sanitary article,
which absorbent element comprises:
a first layer of laminate material, having first cavities;
a plurality of super-absorbent material masses, each super-absorbent material mass of said plurality being received in a respective first cavity of said first layer of laminate material;
a second layer of laminate material, having second cavities, each second cavity being arranged so as to be received in a respective corresponding first cavity of said first layer of laminate material, the convexity of the second cavity facing the concavity of the first cavity and the respective super-absorbent material mass received therein,
wherein said first layer of laminate material and said second layer of laminate material are fixed one another at least at intermediate portions, devoid of said first cavities and said second cavities, and
wherein the overall configuration is such that said super-absorbent material masses are capable of absorbing the biological fluid, by expanding and deforming the respective second cavities up to overturn the concavity and convexity thereof.

2. The absorbent element according to claim 1, wherein said first cavities and said second cavities cooperate to define a seat which receives the respective super-absorbent material mass.

3. The absorbent element according to claim 1, comprising a third laminate material layer coupled to said second layer on a side opposite to a coupling of said second layer with said first layer.

4. The absorbent element according to claim 1, comprising a fourth laminate material layer coupled to said first layer on a side opposite to the coupling of said first layer with said second layer.

5. The absorbent element according to claim 1, wherein said first cavities and said second cavities have the same profile.

6. The absorbent element according to claim 1, wherein said first cavities or said second cavities have a substantially cylindrical profile.

7. The absorbent element according to claim 1, wherein said first cavities or said second cavities have a frusto-conical profile.

8. The absorbent element according to claim 1, wherein said first cavities or said second cavities are obtained by embossing.

9. A sanitary article which comprises one or more absorbent elements according to claim 1.

10. A sanitary article according to claim 9, which is a diaper.

11. An apparatus for manufacturing an absorbent element according to claim 1,
which apparatus comprises:
a first embossing roller, having first protruding elements and configured to be engaged by a first laminate material;
a second embossing roller, having second protruding elements and configured to be engaged by a second laminate material;
a suction roller rotationally coupled to said first embossing roller and, downstream of said first embossing roller, to said second embossing roller, which suction roller has a plurality of openings, each one suitable for receiving a first protruding element of said first protruding elements or a second protruding element of said second protruding elements, and
wherein the configuration is such that, during a coordinated rotation of said first embossing roller and suction roller, a first protruding element engages a respective opening with interposition of the first laminate material so as to form in the first laminate material a respective first cavity,
said suction roller having suction means of super-absorbent material from a reservoir, which suction means exerts a suction through a part of said openings facing, in use, the reservoir, so that a mass of super-absorbent material is sucked within a respective first cavity of the first laminate material; and
wherein the configuration is such that, during a coordinated rotation of said second embossing roller and suction roller downstream of said suction, a second protruding element engages a respective opening with interposition of said first laminate material and of said second laminate material so as to form in the second laminate material a respective second cavity.

12. The apparatus according to claim 11, comprising an auxiliary roller rotationally coupled to said first embossing roller upstream of said suction roller and provided with auxiliary openings each one suitable for receiving a respective protruding element of said first embossing roller, wherein the configuration is such that, during a coordinated rotation of said first embossing roller and auxiliary roller, a first protruding element engages a respective auxiliary opening with interposition of said first laminate material so as to form in said first laminate material a respective additional cavity.

13. The apparatus according to claim 11, wherein said first protruding elements or said second protruding elements or said openings or said auxiliary openings have a cylindrical embossing profile.

14. The apparatus according to claim 11, wherein said first protruding elements or said second protruding elements or said openings or said auxiliary openings have a tapered embossing profile.

15. The apparatus according to any claim 11, comprising a feeding roller of a third laminate material arranged downstream of said second embossing roller.

16. The apparatus according to claim 11, comprising a coupling unit of said first laminate material and said second laminate material.

17. A method for manufacturing an absorbent element according to claim 1, which method provides, in sequence, the following steps:
feeding a first laminate material to a first embossing roller and obtaining in said first laminate material first cavities;
sucking a super-absorbent material mass from a reservoir directly in each one of said first cavities by means of a suction roller rotationally coupled to said first embossing roller and having openings through which said sucking takes place; and
feeding a second laminate material to a second embossing roller and obtaining in said second laminate material second cavities, each one received in a respective first cavity of said first laminate material.

18. The method according to claim 17, comprising a step of coupling said first laminate material and said second laminate material.

19. An absorbent element configured for absorbing biological liquids and configured to be incorporated in a sanitary article,
which absorbent element comprises:
a first layer of laminate material, having first cavities;
a plurality of super-absorbent material masses, each super-absorbent material mass of said plurality being received in a respective first cavity of said first layer of laminate material;
a second layer of laminate material, having second cavities, each second cavity being arranged so as to be received in a respective first cavity of said first layer of laminate material, the convexity of the second cavity facing the concavity of the first cavity and the respective super-absorbent material mass received therein,
wherein said first layer of laminate material and said second layer of laminate material are fixed one another at least at intermediate portions, devoid of said first cavities and said second cavities,
wherein the overall configuration is such that said super-absorbent material masses are capable of absorbing the biological fluid, by expanding and deforming the respective second cavities up to overturn the concavity and convexity thereof, and
wherein each one of said first cavities has a double-bag profile, defining a main compartment and a secondary compartment for housing the respective super-absorbent material mass, said secondary compartment being arranged centrally at a bottom of said main compartment.

20. The absorbent element according to claim 19, wherein each super-absorbent material mass is received at said secondary compartment.

21. The absorbent element according to claim 19, wherein said secondary compartment has a cylindrical or frusto-conical profile.

22. An apparatus for manufacturing an absorbent element, said absorbent element comprising:
a first layer of laminate material, having first cavities;
a plurality of super-absorbent material masses, each super-absorbent material mass of said plurality being received in a respective first cavity of said first layer of laminate material;
a second layer of laminate material, having second cavities, each second cavity being arranged so as to be received in a respective first cavity of said first layer of laminate material, the convexity of the second cavity facing the concavity of the first cavity and the respective super-absorbent material mass received therein,
wherein said first layer of laminate material and said second layer of laminate material are fixed one another at least at intermediate portions, devoid of said first cavities and said second cavities,
wherein the overall configuration is such that said super-absorbent material masses are capable of absorbing the biological fluid, by expanding and deforming the respective second cavities up to overturn the concavity and convexity thereof,
wherein the apparatus comprises:
a first embossing roller, having first protruding elements and configured to be engaged, in use, by a first laminate material;
a second embossing roller, having second protruding elements and configured to be engaged, in use, by a second laminate material;
a suction roller rotationally coupled to said first embossing roller and, downstream of said first embossing roller, to said second embossing roller, which suction roller has a plurality of openings, each one suitable for receiving a first protruding element of said first protruding elements or a second protruding element of said second protruding elements; and
temperature control means of one or more of said first embossing roller, second embossing roller and suction roller,
wherein the configuration is such that, during a coordinated rotation of said first embossing roller and suction roller, a first protruding element engages a respective opening with interposition of the first laminate material so as to form in the first laminate material a respective first cavity,
said suction roller having suction means of super-absorbent material from a reservoir, which suction means exerts a suction through a part of said openings facing, in use, the reservoir, so that a mass of super-absorbent material is sucked within a respective first cavity of the first laminate material; and
wherein the configuration is such that, during a coordinated rotation of said second embossing roller and suction roller downstream of said suction, a second protruding element engages a respective opening with interposition of said first laminate material and of said second laminate material so as to form in the second laminate material a respective second cavity.

23. A method for manufacturing an absorbent element,
said absorbent element comprising:
a first layer of laminate material, having first cavities;
a plurality of super-absorbent material masses, each super-absorbent material mass of said plurality being received in a respective first cavity of said first layer of laminate material;
a second layer of laminate material, having second cavities, each second cavity being arranged so as to be received in a respective first cavity of said first layer of laminate material, the convexity of the second cavity facing the concavity of the first cavity and the respective super-absorbent material mass received therein,
wherein said first layer of laminate material and said second layer of laminate material are fixed one another at least at intermediate portions, devoid of said first cavities and said second cavities,
wherein the overall configuration is such that said super-absorbent material masses are capable of absorbing the biological fluid, by expanding and deforming the respective second cavities up to overturn the concavity and convexity thereof
wherein the method comprises the following steps in sequence:
feeding a first laminate material to a first embossing roller and obtaining in said first laminate material first cavities;
sucking a super-absorbent material mass from a reservoir directly in each one of said first cavities by means of a suction roller rotationally coupled to said first embossing roller and having openings through which said sucking takes place; and feeding a second laminate material to a second embossing roller and obtaining in said second laminate material second cavities, each one received in a respective first cavity of said first laminate material,
wherein said first cavities or said second cavities are obtained by thermoforming.

* * * * *